US012708701B2

(12) United States Patent
Widick et al.

(10) Patent No.: US 12,708,701 B2
(45) Date of Patent: Aug. 18, 2026

(54) SPECIALTY FIBRIN PRODUCT

(71) Applicant: Fibrin, LLC, Delray Beach, FL (US)

(72) Inventors: Mark H. Widick, Boca Raton, FL (US); Abraham Lavi, Delray Beach, FL (US)

(73) Assignee: Fibrin, LLC, FL (US)

( * ) Notice: Subject to any disclaimer, the term of this patent is extended or adjusted under 35 U.S.C. 154(b) by 647 days.

(21) Appl. No.: 18/103,102

(22) Filed: Jan. 30, 2023

(65) Prior Publication Data

US 2023/0398264 A1 Dec. 14, 2023

Related U.S. Application Data

(60) Provisional application No. 63/304,163, filed on Jan. 28, 2022.

(51) Int. Cl.

| | |
|---|---|
| ***A61L 31/04*** | (2006.01) |
| ***A61L 31/14*** | (2006.01) |
| ***C08J 9/00*** | (2006.01) |
| ***C08J 9/30*** | (2006.01) |
| ***C08L 89/00*** | (2006.01) |

(52) U.S. Cl.

CPC ........... *A61L 31/046* (2013.01); *A61L 31/047* (2013.01); *A61L 31/146* (2013.01); *A61L 31/148* (2013.01); *C08J 9/0066* (2013.01); *C08J 9/30* (2013.01); *C08L 89/00* (2013.01); *A61L 2430/40* (2013.01); *C08J 2207/10* (2013.01); *C08J 2389/00* (2013.01); *C08L 2201/06* (2013.01); *C08L 2203/02* (2013.01); *C08L 2203/14* (2013.01)

(58) Field of Classification Search

CPC .. A61L 2430/40; A61L 31/046; A61L 31/047; A61L 31/146; A61L 31/148; C08J 2207/10; C08J 2389/00; C08J 9/0066; C08J 9/30; C08L 2201/06; C08L 2203/02; C08L 2203/14; C08L 89/00

See application file for complete search history.

(56) References Cited

U.S. PATENT DOCUMENTS

2004/0071786 A1* 4/2004 Grippi .................. A61L 24/106 424/530

* cited by examiner

*Primary Examiner* — Jennifer Wecker
*Assistant Examiner* — Jonathan Bortoli
(74) *Attorney, Agent, or Firm* — Barbara E. Johnson, Esq.

(57) ABSTRACT

The present invention is a specially prepared fibrin foam, and a method of (and equipment for) making it, which is flexible, contains either open cells, closed cells or both, and having individual cell diameters between 0.001 and 2 mm. Typical ratios of reactants, to give the desired foam characteristics, include 50 cc (45-55 cc) of whole blood (prior to separation to the plasma component) with the subsequent addition thereto of 2 ml (1.5-2.5 ml) 3% hydrogen peroxide, 5000 units (4500-5500 units) thrombin and 1 gm (0.9-1.1 g) calcium chloride in 3 cc (2-4 cc) water. The present invention also includes specialty vessels and constructs, namely, automated, or semi-automated inner containers for the non-blood reactants, and a custom outer separation vessel having a punted based with an annular base lip as well as an upper tube shape tapering inward towards its top annular opening.

3 Claims, 3 Drawing Sheets

SPECIALTY FIBRIN PRODUCT

CROSS-REFERENCE TO RELATED APPLICATION

This patent application claims priority to, and incorporates herein by reference, U.S. Provisional Patent Application No. 63/304,162 filed 28 Jan. 2022.

BACKGROUND OF THE INVENTION

Fibrin, a natural product whose constituents are ubiquitous in many humans and animal blood and tissue sources, has a storied history as a base material or substance for implantation, wound healing, and so forth. Much is known about fibrin and its related biological molecules including but not limited to thrombin. Prior art uses for fibrin have been somewhat limited, however, due to a general lack of finesse in how to collect, generate, treat, and use fibrin from any sources, including but not limited to autologous sources. Soluble fibrinogen is the precursor molecule of the insoluble polymer fibrin through the enzymatic cleavage, by thrombin in the presence of calcium ions. Past attempts to create fibrin foam suffered from the need for concentrated fibrinogen solutions, pooled sourced plasma and lengthy processing times.

In the meantime, the need for surgically implantable foams or gels has soared in recent years, as so many new structure reconstructions are now possible to the human body (if only they could be kept perfectly in place until they heal). As a single example, it is now possible to reconstruct a human eardrum by harvesting (ideally as an autologous graft) a small piece of the patient's fascia, briefly drying it and placing it in the ear canal in the area of the original eardrum. The fascia will graft itself in place over a period of several days, and replicate the function of a natural eardrum beautifully, but the challenge is—how can the surgeon keep the fascia material in place until the new eardrum is securely grafted? Stitching it in place—is out of the question. Traditional packing materials intended to keep the fascia in place have more or less tended to fail—they become wet, soggy, and tend to slump or dislocate, especially because the patient cannot possibly hold his or her head completely still for several days after ear surgery. Barometric forces, from biological processes including auto inflation of the Eustachian tube, external pressure from changes in altitude flying in aircraft, can result in dislocation forces on the tissue graft. A material with both compressive recoil from external deformation and surface adhesive properties, would be ideal in many surgical and healing applications. For such, and infinite other applications where a hemostasis or structural scaffold is needed, the surgeon needs an implantable foam, autologous but not always, that will hold its shape and form during the patient's recovery time but then will dissolve and reabsorb thereafter. When the foam is an autologous fibrin foam, the likelihood for rejection or allergic reactions will be eliminated. When the foam is produced from donated blood or plasma, the allergen and rejection profiles are still more favorable than foams made of porcine, gelatin, or other xenographic materials.

A need remains, therefore, for a surgically implantable fibrin foam, generally but not necessarily an autologous foam, that will hold its shape and constitution for several days to weeks after creation and implantation (2-8 weeks), but thereafter will be reabsorbed harmlessly within the patient's body, regardless of the location of its implantation.

SUMMARY OF THE INVENTION

In order to meet this need, the present invention is a specially prepared fibrin foam, which is flexible, contains either open cells, closed cells or both, and having individual cell diameters between 0.001 and 2 mm. By "fibrin foam" is meant that the predominant constituent of the foam is fibrin, most often originating from constituents in human blood plasma, whether autologous or donated/harvested. The fibrin foam has an elastic recovery of about 10-100 times its own weight, and a compression resistance of a similar magnitude. Due to the method of its preparation, the present fibrin foam is able to maintain its physical structure for between 2-8 weeks, which makes it ideal for implantations in situations where fine structural stabilization is needed, as well as myriad other applications in which fibrin foam can be endlessly useful, including but not limited to hemostasis, skin graft sculpting, burn dressing and treatment, and other medical and surgical applications. One key to making the present fibrin foams is to assure the correct inclusion of the proper amount of air, or other appropriate gas, into the final foam, unlike the many fibrin "glue" or stiff "pad" surgical products already developed in the past. The present method therefore importantly collects blood or plasma, adds 4% citrate thereto, centrifuges the blood or plasma to remove any red blood cells (or most of them), and adds all of hydrogen peroxide, human thrombin and calcium chloride in particular amounts to achieve a specialized fibrin foam from the starting separated plasma. While in many instances, the use of autologous blood for a patient foam implant can be ideal, the present invention may also be –100-used with donor (or otherwise harvested) plasma or blood. Typical ratios of reactants, to give the desired foam characteristics, include 50 cc (45-55 cc) of whole blood (prior to separation to the plasma component) with the subsequent addition thereto of 2 ml (1.5-2.5 ml) 3% hydrogen peroxide, 5000 units (4500-5500 units) human thrombin and 1 gm (0.9-1.1 g) calcium chloride in 3 cc (2-4 cc) water. The use of these reactants and amounts gives a superior fibrin foam which can "stand up" to duty as a structural surgical implant, is reversibly compressible enough to use as a packing material, and yet which will dissolve and resorb in approximately 2-8 weeks from implantation. The present invention also includes specialty vessels and constructs which give new and unexpected results in carrying out the method, namely, automated containers for releasing the non-blood reactants and a custom centrifuge separation vessel having a punted based with an annular base lip, as well as a shape tapering inwards towards its top opening. These constructs simplify the production and add unique means of manipulating properties of the final fibrin foam products.

BRIEF DESCRIPTION OF THE DRAWINGS

FIG. 1(*b*) is a side elevational view of the outside of the specialized centrifuge vessel 10.

FIG. 1(*c*) is a side sectional view of the specialized centrifuge vessel 10, showing its flat-convex raised bottom as well as the raised "lip."

DETAILED DESCRIPTION OF THE INVENTION

In addition to the key reactants and amounts to make the present fibrin foam, together with the concomitant (s) therefor, the present invention also includes specialized reaction vessels to optimize preparation of the foam in, for example, an operating room setting in real time. Therefore, the present invention not only embraces the above-described reactants and amounts but includes the use of specialized vessels and hardware which facilitate a mostly-if-not-completely "hands off" approach (other than initial phlebotomy) to turning a patient (or donor) blood sample into fibrin foam, right in the surgical center or hospital operating room, and at the time it is needed.

Figure 1A:
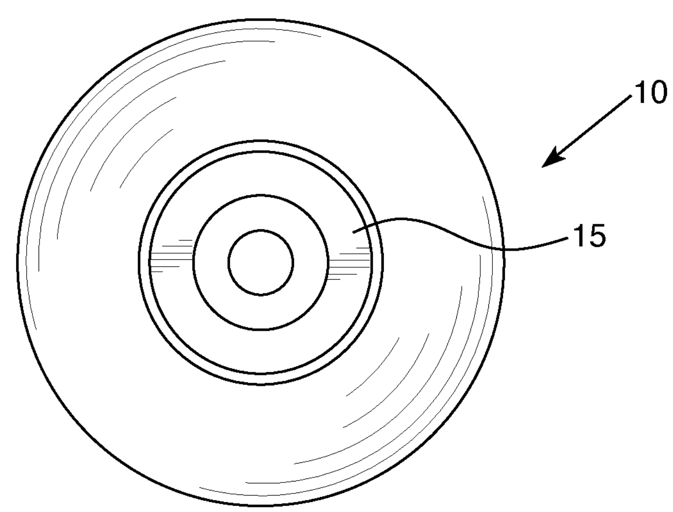
FIG. 1(*a*) is a plan view of a specialized centrifuge vessel 10.
Figure 1B:
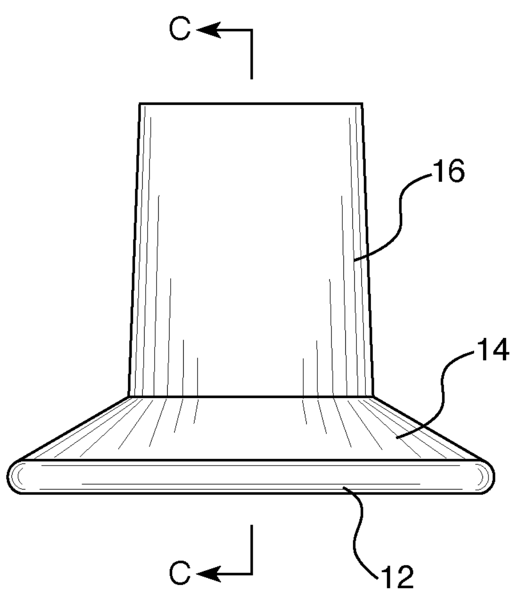
Figure 1C:
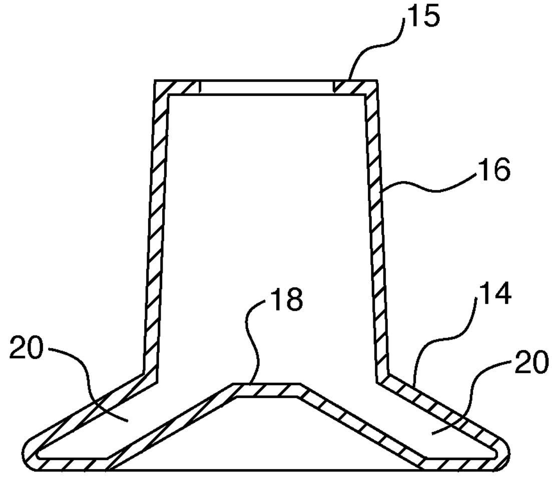

The main overall equipment used to facilitate the present method is a tabletop centrifuge, to which (in one embodiment) a particularly designed centrifuge vessel beneficially expedites the desired fibrin foam formation as described further below. While standard centrifuge tubes may be used in a standard centrifuge, usually six or eight tubes per centrifuge cavity, the specialized centrifuge vessel of FIG. 1 is designed to be mounted in a centrifuge vertically, with the center of rotation of the centrifuge's being positioned directly through the center vertical axis of the vessel. Such a specialized centrifuge vessel according to the invention is shown in FIG. 1 (FIGS. 1 (*a*)-(*c*)) as vessel 10. Referring now to FIG. 1, FIG. 1(*a*) illustrates a plan view of a specialized centrifuge vessel 10, with FIG. 1(*b*) showing a side elevational view of the outside of that vessel and its wide base wall 12, frustoconical base segment 14 and inwardly tapering tube 16. The sectional view of the vessel 10 in FIG. 1(*c*) further shows the flat-convex raised bottom of the interior of the vessel ("punt" 18) as well as the base "lip" 20 structures of the vessel, which allow liquid inside the vessel 10 to form an annulus within the frustoconical base segment 14. (By "flat-convex" is meant either a curved or an annular punt shape to create a raised inner base wall of vessel 10. Any sort of known "punt" is useful in the context of the present invention) The centrifuge vessel 10 of FIG. 1 is versatile—due to its shape the non-blood reactants of the present invention may be manually added to the upper opening of the vessel after blood is separated into is plasma and red-blood-cell components, or a second interior tube containing non-blood reactants may be positioned therein as shown in FIGS. 2-5, further discussed below. The reactants may be added to the plasma through the top opening of the vessel after the centrifuge comes to rest or while it is still spinning. This embodiment eliminates the need for the reactant delivery device from coming into contact with the vessel containing the plasma. The shape of the inwardly tapering tube 16 of vessel 10 is essential for good separation of whole blood into plasma and red cells—the taper forces the denser red blood cells down into the aforementioned annulus within the frustoconical base segment 14, since the denser red blood cells cannot remain in place on the inwardly tapering tube 16 during centrifuging, leaving a good separation of plasma in the upper portion of the vessel 10 after centrifuging is complete. Generally, because the radius of the vessel is smaller than the radius at which the blood sample in multiple tubes rotates in a conventional centrifuge, a higher RPM for the proposed vessel would be necessary to achieve efficient plasma separation. Those skilled in the art know how many RPM and how long to run a centrifuge to obtain separation of plasma from red blood cells, regardless of whether an array of tubes or a single center axis vessel is used.

Figures 2, 3:
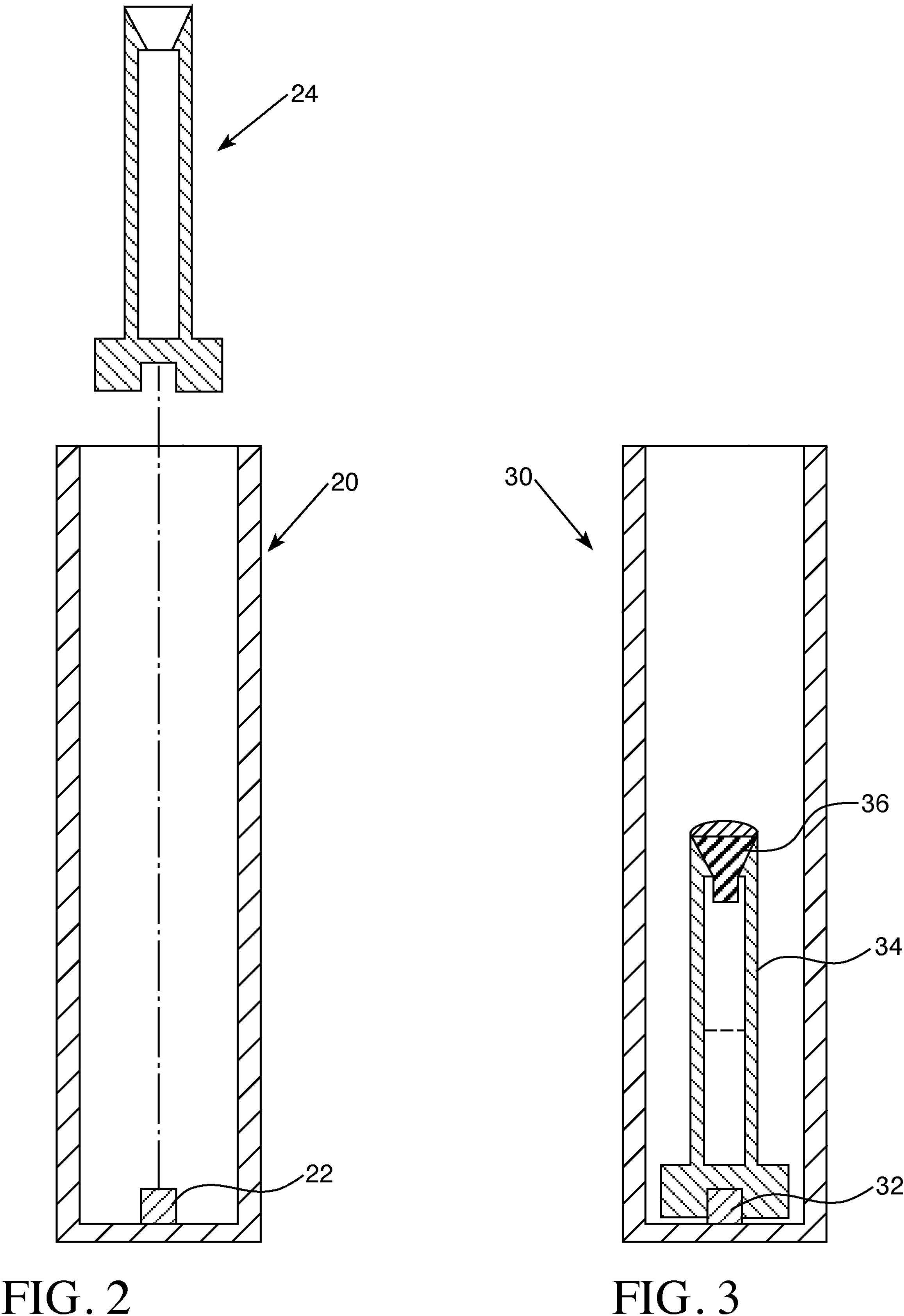
FIG. 2 is a side sectional view of a centrifuge tube with a reaction chamber in exploded view.
FIG. 3 is a side sectional view of a centrifuge tube with a reaction chamber secured therein.

Referring now to FIGS. 2 and 3, a standard cylindrical centrifuge tube (any standard tube) may alternatively be outfitted with an interior add-on reactant chamber as shown, or the vessel 10 of FIG. 1 may be outfitted with an interior add-on reactant chamber as shown in FIGS. 2-3. Referring now to FIG. 2, a threaded post 22 within the outer centrifuge tube 20 engages an inner add-on reactant chamber 24, which before charging to the outer centrifuge tube is pre-loaded with the present non-blood reactants (hydrogen peroxide, human thrombin, and calcium chloride solution). By creating a combination reaction array of this type, the admixing of the blood plasma and the reactants, according to the present method, may be mostly or fully automated in the operating room or other care facility. Referring now to FIG. 3, the cap 36 of the inner add-on reactant chamber 34 (within outer centrifuge tube 30 having threaded post 32) can be solenoid triggered or radio controlled (or governed any other way, for example changing RPM) to open at a predetermined or any desired time, to bring the plasma (as separated in the tube) and hydrogen peroxide, human thrombin and calcium chloride (within the inner chamber) into contact with one another to create the present fibrin foam. Alternatively, using multiple tube feeders from a central chamber of the admixture of reactant to inject the reactants into the individual tubes containing plasma. This distribution mechanism and the central chamber of the reactants can be non-rotating. Decomposition of the hydrogen peroxide generates oxygen, which in turn facilitates foam formation. Interestingly, the incidental presence of trace amounts of residual red blood cells is actually desirable, in the plasma fraction, because the residual red blood cells contain the enzyme catalase ensuring the full decomposition of the hydrogen peroxide and, in turn, the full mixing and foam formation of all the admixed reactants. This is true regardless of whether reaction chambers of FIGS. 1-3 are used.

With further reference to FIGS. 2 and 3, the use of the inner add-on reactant chamber 24, 34—put in place before charging patient blood or plasma in, or donor blood or plasma around it—means that the outer reaction vessel is particularly easy and safe to use. Except to charge the 50 cc or so of patient blood, collected by standard phlebotomy at the time of use (with the added standard anticoagulant), the vessel "is ready to go" as soon as the blood or plasma has been added, particularly when the outer vessel or outer tube has been previously fitted with the inner add-on reactant chamber 24, 34 having the above-described reactants already charged thereto. All of the vessels and tubes of the present disclosure are intended to be disposable, that is, single use.

Figure 4:
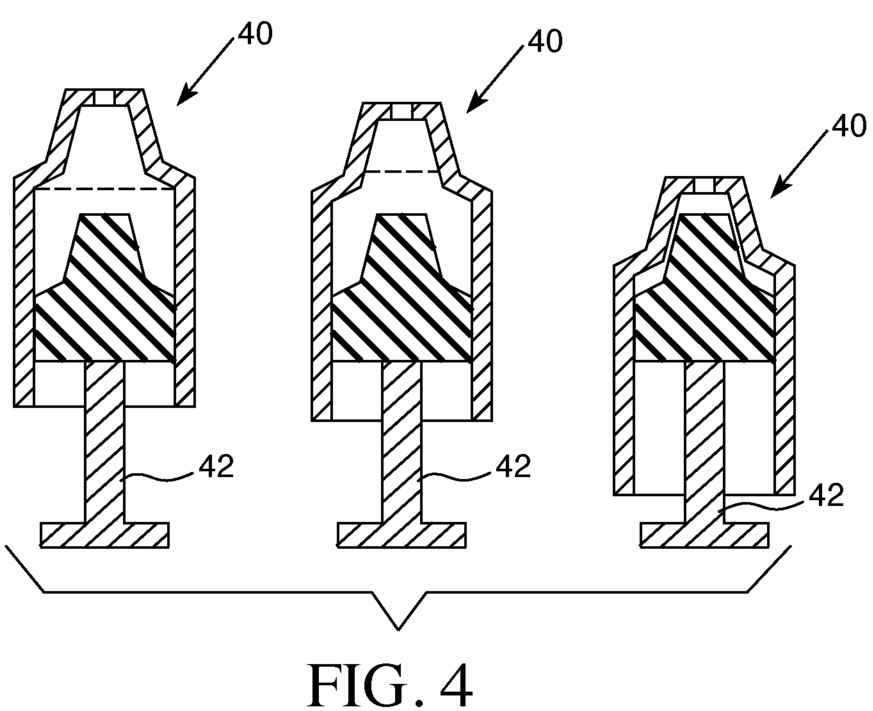
FIG. 4 is a side sectional view of an actuatable syringe.
Figure 5:
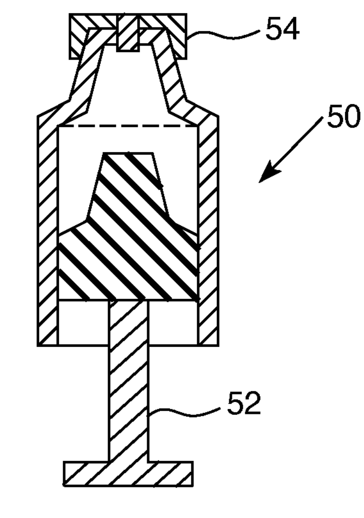
FIG. 5 is a side sectional view of an actuatable syringe with an optional cap.

Referring now to FIGS. 4 and 5, instead of an inner add-on unit that opens due to remote actuation of its cap, an analogous syringe containing the non-blood reactants may be placed in the bottom of the reaction vessel or tube and set to discharge its contents upon exertion of a predetermined force under centrifuge. Gravity may initially hold the syringe in place, or a comparable threaded post and receiving aperture may be provided as shown in FIG. 1, to secure the syringe in position. The syringe 40, 50 has a plunger 42, 52 thereon, with (as shown in FIG. 5) an optional cap 54. The calibrating of the syringe to the centrifuge is well within the skill of the art of separating whole blood into plasma, and the reactants in the syringe are released at the predetermined RPM and time by adjusting the compression force of the syringe to match when the plasma will have been separated.

Variation in the above hardware is possible after one understands the ingenuity described above. The adjustment of standard test tubes to a tapering shape, for optimal separation of red blood cells from plasma, is within the scope of the invention. Even the manual preparation of fibrin foam according to the present method is within the scope of the invention, although clearly for commercial and safety applications the use of single-use, disposable vessels or tubes is optimal, particularly because blood products are involved. The trace amounts of red blood cells that actually help the formation of the fibrin foam are in an amount of about 0.5-1.5% of the weight of the plasma.

After the method, described above, is used to create a foamed fibrin product, the following are expected. Overall centrifuging time can be within about 5-15 minutes and the reaction time among the plasma and non-blood reactants occurs over a period between 4-8 minutes. After 4-8 minutes, a soft, still-wet fibrin foam can be extracted from the tube or vessel with any standard tool—a sterile glass rod is ideal—and typically should be placed on a sterile absorbent surface to cure for approximately 5-30 minutes before use. If desired, the sterile absorbent surface can be illuminated by a surgical light to enhance curing of the foam. Fibrin foams prepared according to the above methods and parameters will not cure to any sort of rigid construct when cured for less than one hour, so typically the present fibrin foam constructs are used within about 10-50 minutes after their creation. After initial curing, the foam product may be cut with a sterile surgical scalpel, or scissors, to any desired shape. The fibrin foam of the present invention, with its inherent malleability, may be used as compressible packing material as well as structural scaffolding, in any appropriate surgical setting. When the fibrin foam of the present invention has been made from autologous patient blood, the only fibrin being reintroduced, surgically, into the patient—is the patient's own fibrin.

Additional aspects of the invention should be understood as follows. When the vessel or tubes are still spinning in a centrifuge, upon manual or automated addition of the additional non-blood reactants, a better-quality fibrin foam results than if the separated plasma and reactants are admixed manually, after centrifuging. While not wishing to be bound thereby, the theory behind this phenomenon is that the fluid dynamics and motion within the plasma that occur during continued centrifuging encouraging better and more thorough mixing than a manual stirring protocol of the reactants could achieve. For this reason, certain embodiments of the invention do provide for the automated, or semi-automated, admixing of the non-blood reactants with the blood components, while the centrifuge is still running to separate the plasma from the red blood cells in the first place. Another reason why the reaction, while the centrifuge is still running, is believed to work so well is—while separating plasma from red blood cells, any separation of the two may collapse or revert after the centrifugal force is removed. Keeping the centrifuge running while introducing the non-blood reactants maximizes the efficacy of separation of the plasma from the blood, therefore. Given the helpful chemical reaction of a small fraction of red cells in the plasma, however, as discussed above the present invention definitely embraces the mechanical introduction of non-blood reactants after the whole blood has been centrifugally separated. Operational finesse among these parameters is within the skill of the art, given the above explanation.

To repeat, the vessel 10 of FIG. 1 is provided to a centrifuge as a single vessel for rotation, affixed to rotate along its vertical axis. The more standard centrifuge tubes of FIGS. 2-3 are meant for alternative use in a centrifuge equipped to spin an array of tubes at once—usually 6 or 8 tubes in a "sunburst" array known in the art. These more traditional centrifuge arrays are usually referred to as "baskets," which hold a multitude of tubes therein.

Although the invention has been described with particularity above, with specific mention of constituents, amounts, method steps, vessels, tubes and physical structures, the invention is only to be limited insofar as is set forth in the accompanying claims. The numerical data mentioned in the claims listed herein should be understood as representative of the proportions of the necessary reactants necessary to produce fibrin foam having the desired properties described above, and amounts can be scaled up or down as needed, usually but not necessarily limited to 0.1 to 1000 times the amounts in proportion. In certain occasions, entrained air can be substituted for the addition of hydrogen peroxide discussed above, to achieve an open cell, closed cell (or both) foam product. The initial blood sample may vary from case to case depending on the volume of fibrin foam needed for the specific procedure. Accordingly, the volume and weight of each reactant would be scaled according to the blood sample size on hand. Most adults could easily tolerate phlebotomy sample larger than 50 cc with minimal adverse effects. We need only to scale the device or repeat the process multiple times. The larger scaled up amounts referenced above would more typically be from donated or harvested plasma, rather than individual patients for which autologous product is desired.

We claim:

1. A method of producing a medical fibrin foam, the method comprising:

collecting a whole blood sample having a volume between 45 and 55 cc from a subject;

separating a plasma fraction from the whole blood sample by centrifuging the whole blood sample;

forming a reaction mixture by admixing into the plasma fraction;

a volume of water between 2 and 4 cc;

a volume of 3% hydrogen peroxide between 1.5 and 2.5 ml;

an amount of thrombin between 4,500 and 5,500 units;

an amount of calcium chloride between 0.9 and 1.1 g;

forming a quantity of fibrin foam from the reaction mixture;

separating the quantity of fibrin foam from unreacted constituents of the reaction mixture; and obtaining the medical fibrin foam by curing the quantity of fibrin foam.

2. The method according to claim 1, wherein the curing has a duration between 5 and 60 minutes.

3. The method according to claim 1, wherein the volume of the collected whole blood sample is 55 cc, the volume of admixed 3% hydrogen peroxide is 2 ml, the amount of the admixed thrombin is 5,000 units, and the amount of the admixed calcium chloride is 1 g.

* * * * *